(12) United States Patent  (10) Patent No.: US 9,257,220 B2
Nicholls et al.  (45) Date of Patent: Feb. 9, 2016

(54) MAGNETIZATION DEVICE AND METHOD (71) Applicant: eZono AG, Jena (DE)

(72) Inventors: Robert Nicholls, Jena (DE); Eliseo Sobrino, Jena (DE)

(73) Assignee: eZono AG, Jena (DE)

( * ) Notice: Subject to any disclaimer, the term of this patent is extended or adjusted under 35 U.S.C. 154(b) by 0 days.

(21) Appl. No.: 13/786,060

(22) Filed: Mar. 5, 2013

(65) Prior Publication Data

US 2014/0253270 A1  Sep. 11, 2014

(51) Int. Cl.
H01F 7/20 (2006.01)
H01F 13/00 (2006.01)
A61B 5/06 (2006.01)
A61M 5/42 (2006.01)

(52) U.S. Cl.
CPC .............. *H01F 13/003* (2013.01); *A61B 5/062* (2013.01); *A61M 5/427* (2013.01); *A61M 2205/0272* (2013.01); *A61M 2205/3306* (2013.01); *A61M 2205/50* (2013.01)

(58) Field of Classification Search
CPC ........ A61B 5/062; A61B 5/06; H01F 13/003; H01F 13/00
USPC .................................................. 335/284, 285
See application file for complete search history.

(56) References Cited

U.S. PATENT DOCUMENTS

| 4,317,078 | A | | 2/1982 | Weed | |
|---|---|---|---|---|---|
| 4,508,119 | A | * | 4/1985 | Tukamoto | ..................... 606/189 |
| 5,042,486 | A | | 8/1991 | Pfeiler | |
| 5,055,813 | A | * | 10/1991 | Johnson | ........................ 335/284 |
| 5,425,382 | A | | 6/1995 | Golden | |
| 5,622,169 | A | | 4/1997 | Golden | |
| 5,744,953 | A | | 4/1998 | Hansen | |
| 5,767,669 | A | | 6/1998 | Hansen | |
| 5,831,260 | A | | 11/1998 | Hansen | |
| 5,833,608 | A | | 11/1998 | Acker | |

(Continued)

FOREIGN PATENT DOCUMENTS

| AT | 455499 | 2/2010 |
|---|---|---|
| AT | 492214 | 1/2011 |

(Continued)

OTHER PUBLICATIONS

Stolowitz Ford Cowger LLP, Listing of Related Cases (Updated); Portland, OR; Sep. 17, 2014; 1 pages.

(Continued)

*Primary Examiner* — Bernard Rojas
(74) *Attorney, Agent, or Firm* — Schwabe, Williamson & Wyatt (57) ABSTRACT

A magnetizer for a tissue-penetrating medical tool such as a needle, cannula, stylet, or catheter consist of a magnetic flux generator which generates a magnetic field in a tool-receiving space. The tool can be passed through or into and out of the space to magnetize it. Optionally the space can be defined by a disposable plastics tube, with a closed end, so that a defined length of the tool is magnetized. The magnetic flux generator can be a permanent magnet or electromagnet. Alternatively a conveyor belt can be used to transport a tissue-penetrating medical tool through a magnetic field generated by an electromagnet with the belt and the electromagnetic being controlled in response to an optical sensor for detecting the position of the tissue-penetrating medical tool. The device is suitable for magnetizing tools for use in surgical procedures where the tool is to be magnetically tracked.

29 Claims, 4 Drawing Sheets (56) References Cited

U.S. PATENT DOCUMENTS

| | | |
|---|---|---|
| 5,879,297 A | 3/1999 | Haynor |
| 5,902,238 A | 5/1999 | Golden |
| 5,941,889 A | 8/1999 | Cermak |
| 5,944,023 A | 8/1999 | Johnson |
| 5,953,683 A | 9/1999 | Hansen |
| 6,073,043 A | 6/2000 | Schneider |
| 6,172,499 B1 | 1/2001 | Ashe |
| 6,216,028 B1 | 4/2001 | Haynor |
| 6,233,476 B1 | 5/2001 | Strommer |
| 6,246,231 B1 | 6/2001 | Ashe |
| 6,246,898 B1 | 6/2001 | Vesely |
| 6,248,074 B1 | 6/2001 | Ohno |
| 6,263,230 B1 | 7/2001 | Haynor et al. |
| 6,266,551 B1 | 7/2001 | Osadchy |
| 6,310,532 B1* | 10/2001 | Santa Cruz et al. ........... 335/284 |
| 6,361,499 B1 | 3/2002 | Bates |
| 6,368,280 B1 | 4/2002 | Cermak |
| 6,379,307 B1 | 4/2002 | Filly |
| 6,427,079 B1 | 7/2002 | Schneider |
| 6,438,401 B1 | 8/2002 | Cheng |
| 6,528,991 B2 | 3/2003 | Ashe |
| 6,542,766 B2 | 4/2003 | Hall |
| 6,546,279 B1 | 4/2003 | Bova |
| 6,587,709 B2 | 7/2003 | Solf |
| 6,626,832 B1 | 9/2003 | Paltieli |
| 6,669,635 B2 | 12/2003 | Kessman |
| 6,678,552 B2 | 1/2004 | Pearlman |
| 6,690,159 B2 | 2/2004 | Burreson et al. |
| 6,690,963 B2 | 2/2004 | Ben-Haim |
| 6,716,166 B2 | 4/2004 | Govari |
| 6,733,458 B1 | 5/2004 | Steins et al. |
| 6,754,596 B2 | 6/2004 | Ashe |
| 6,774,624 B2 | 8/2004 | Anderson |
| 6,784,660 B2 | 8/2004 | Ashe |
| 6,785,571 B2 | 8/2004 | Glossop |
| 6,788,967 B2 | 9/2004 | Ben-Haim |
| 6,813,512 B2 | 11/2004 | Aldefeld |
| 6,834,201 B2 | 12/2004 | Gillies |
| 6,856,823 B2 | 2/2005 | Ashe |
| 6,895,267 B2 | 5/2005 | Panescu |
| 6,954,128 B2* | 10/2005 | Humphries et al. .......... 335/306 |
| 6,980,921 B2 | 12/2005 | Anderson |
| 7,020,512 B2 | 3/2006 | Ritter |
| 7,048,745 B2 | 5/2006 | Tierney |
| 7,090,639 B2 | 8/2006 | Govari |
| 7,197,354 B2 | 3/2007 | Sobe |
| 7,215,990 B2 | 5/2007 | Feussner |
| 7,274,325 B2 | 9/2007 | Fattah |
| 7,275,008 B2 | 9/2007 | Plyvänäinen |
| 7,324,915 B2 | 1/2008 | Altmann |
| 7,351,205 B2 | 4/2008 | Szczech |
| 7,373,271 B1 | 5/2008 | Schneider |
| 7,386,339 B2 | 6/2008 | Strommer |
| 7,471,202 B2 | 12/2008 | Anderson |
| 7,505,810 B2 | 3/2009 | Harlev |
| 7,517,318 B2 | 4/2009 | Altmann |
| 7,524,320 B2 | 4/2009 | Tierney |
| 7,551,953 B2 | 6/2009 | Lardo |
| 7,555,330 B2 | 6/2009 | Gilboa |
| 7,558,616 B2 | 7/2009 | Govari |
| 7,561,051 B1 | 7/2009 | Kynor |
| 7,573,258 B2 | 8/2009 | Anderson |
| 7,588,541 B2 | 9/2009 | Floyd |
| 7,603,155 B2 | 10/2009 | Jensen |
| 7,603,160 B2 | 10/2009 | Suzuki |
| 7,610,078 B2 | 10/2009 | Willis |
| 7,618,374 B2 | 11/2009 | Barnes |
| 7,636,595 B2 | 12/2009 | Marquart |
| 7,652,259 B2 | 1/2010 | Kimchy |
| 7,657,298 B2 | 2/2010 | Moctezuma de la Barrera |
| 7,660,623 B2 | 2/2010 | Hunter |
| 7,668,583 B2 | 2/2010 | Fegert |
| 7,671,887 B2 | 3/2010 | Pescatore |
| 7,697,973 B2 | 4/2010 | Strommer |
| 7,706,860 B2 | 4/2010 | McGee |
| 7,722,565 B2 | 5/2010 | Wood |
| 7,749,168 B2 | 7/2010 | Maschke |
| 7,769,427 B2 | 8/2010 | Shachar |
| 7,797,032 B2 | 9/2010 | Martinelli |
| 7,809,421 B1 | 10/2010 | Govari |
| 7,819,810 B2 | 10/2010 | Stringer |
| 7,822,464 B2 | 10/2010 | Maschke |
| 7,831,096 B2 | 11/2010 | Williamson, Jr. |
| 7,835,785 B2 | 11/2010 | Scully |
| 7,840,251 B2 | 11/2010 | Glossop |
| 7,840,253 B2 | 11/2010 | Tremblay |
| 7,840,256 B2 | 11/2010 | Lakin |
| 7,873,401 B2 | 1/2011 | Shachar |
| 7,881,769 B2 | 2/2011 | Sobe |
| 7,907,989 B2 | 3/2011 | Borgert |
| 7,909,815 B2 | 3/2011 | Whitmore, III |
| 7,926,776 B2 | 4/2011 | Cermak |
| 7,945,309 B2 | 5/2011 | Govari |
| 7,962,196 B2 | 6/2011 | Tuma |
| 7,966,057 B2 | 6/2011 | Macaulay |
| 7,971,341 B2 | 7/2011 | Dukesherer |
| 7,974,680 B2 | 7/2011 | Govari |
| 7,996,059 B2 | 8/2011 | Porath |
| 8,023,712 B2 | 9/2011 | Ikuma |
| 8,027,714 B2 | 9/2011 | Shachar |
| 8,041,411 B2 | 10/2011 | Camus |
| 8,041,412 B2 | 10/2011 | Glossop |
| 8,041,413 B2 | 10/2011 | Barbagli |
| 8,049,503 B2 | 11/2011 | Kimura |
| 8,060,184 B2 | 11/2011 | Hastings |
| 8,064,985 B2 | 11/2011 | Peterson |
| 8,068,897 B1 | 11/2011 | Gazdzinski |
| 8,073,529 B2 | 12/2011 | Cermak |
| 8,082,022 B2 | 12/2011 | Moctezuma de la Barrera |
| 8,086,298 B2 | 12/2011 | Whitmore, III |
| 8,088,070 B2 | 1/2012 | Pelissier |
| 8,090,168 B2 | 1/2012 | Washburn |
| 8,106,905 B2 | 1/2012 | Markowitz |
| 8,147,408 B2 | 4/2012 | Bunce |
| 8,162,821 B2 | 4/2012 | Kawano |
| 8,175,680 B2 | 5/2012 | Panescu |
| 8,216,149 B2 | 7/2012 | Oonuki et al. |
| 8,226,562 B2 | 7/2012 | Pelissier |
| 8,228,028 B2 | 7/2012 | Schneider |
| 8,506,493 B2 | 8/2013 | Ostrovsky |
| 2003/0036695 A1 | 2/2003 | Govari |
| 2004/0047044 A1 | 3/2004 | Dalton |
| 2004/0051610 A1* | 3/2004 | Sajan ........................... 335/284 |
| 2004/0106869 A1 | 6/2004 | Tepper |
| 2004/0147920 A1 | 7/2004 | Keidar |
| 2004/0171934 A1 | 9/2004 | Khan |
| 2005/0020919 A1 | 1/2005 | Stringer |
| 2005/0033315 A1 | 2/2005 | Hankins |
| 2005/0101876 A1 | 5/2005 | Pearlman |
| 2005/0107870 A1 | 5/2005 | Wang |
| 2005/0143648 A1 | 6/2005 | Minai |
| 2005/0197569 A1 | 9/2005 | McCombs |
| 2006/0061354 A1 | 3/2006 | Wallance |
| 2006/0072843 A1 | 4/2006 | Johnston |
| 2006/0241397 A1 | 10/2006 | Govari |
| 2006/0253107 A1 | 11/2006 | Hashimshony |
| 2007/0016013 A1 | 1/2007 | Camus |
| 2007/0027390 A1 | 2/2007 | Maschke et al. |
| 2007/0055468 A1 | 3/2007 | Pylvänäinen |
| 2007/0163367 A1 | 7/2007 | Sherman |
| 2007/0167801 A1 | 7/2007 | Webler |
| 2007/0185398 A1 | 8/2007 | Kimura |
| 2007/0276240 A1 | 11/2007 | Rosner |
| 2008/0033286 A1 | 2/2008 | Whitmore |
| 2008/0071172 A1 | 3/2008 | Bruck |
| 2008/0094057 A1 | 4/2008 | Ashe |
| 2008/0134727 A1 | 6/2008 | May |
| 2008/0146939 A1 | 6/2008 | McMorrow |
| 2008/0183071 A1 | 7/2008 | Strommer |
| 2008/0249395 A1 | 10/2008 | Shachar |
| 2008/0262338 A1 | 10/2008 | Paitel |
| 2009/0105581 A1 | 4/2009 | Widenhorn |
| 2009/0105584 A1 | 4/2009 | Jones |
| 2009/0105779 A1 | 4/2009 | Moore |

(56) References Cited

U.S. PATENT DOCUMENTS

| | | |
|---|---|---|
| 2009/0156926 A1 | 6/2009 | Messerly et al. |
| 2009/0228019 A1 | 9/2009 | Gross |
| 2009/0275833 A1 | 11/2009 | Ikeda |
| 2009/0287443 A1 | 11/2009 | Jascob |
| 2009/0299142 A1 | 12/2009 | Uchiyama |
| 2009/0299176 A1 | 12/2009 | Gleich |
| 2009/0312629 A1 | 12/2009 | Razzaque |
| 2009/0322323 A1 | 12/2009 | Brazdeikis |
| 2009/0326323 A1 | 12/2009 | Uchiyama |
| 2010/0049033 A1 | 2/2010 | Kawano |
| 2010/0049050 A1 | 2/2010 | Pelissier |
| 2010/0079158 A1 | 4/2010 | Bar-Tal |
| 2010/0121189 A1 | 5/2010 | Ma |
| 2010/0121190 A1 | 5/2010 | Pagoulatos |
| 2010/0137705 A1 | 6/2010 | Jensen |
| 2010/0156399 A1 | 6/2010 | Chiba |
| 2010/0174176 A1 | 7/2010 | Nagel |
| 2010/0191101 A1 | 7/2010 | Lichtenstein |
| 2010/0249576 A1 | 9/2010 | Askarinya et al. |
| 2010/0268072 A1 | 10/2010 | Hall |
| 2010/0312113 A1 | 12/2010 | Ogasawara |
| 2011/0021903 A1 | 1/2011 | Strommer |
| 2011/0028848 A1 | 2/2011 | Shaquer |
| 2011/0034806 A1 | 2/2011 | Hartov |
| 2011/0054293 A1 | 3/2011 | Markowitz |
| 2011/0060185 A1 | 3/2011 | Ikuma |
| 2011/0081063 A1 | 4/2011 | Leroy |
| 2011/0082366 A1 | 4/2011 | Scully |
| 2011/0118590 A1 | 5/2011 | Zhang |
| 2011/0137152 A1 | 6/2011 | Li |
| 2011/0137156 A1 | 6/2011 | Razzaque |
| 2011/0144476 A1 | 6/2011 | Jolesz |
| 2011/0144524 A1 | 6/2011 | Fish |
| 2011/0184690 A1 | 7/2011 | Iida |
| 2011/0224537 A1 | 9/2011 | Brunner |
| 2011/0230757 A1 | 9/2011 | Elgort |
| 2011/0237945 A1 | 9/2011 | Foroughi |
| 2011/0251607 A1 | 10/2011 | Kruecker |
| 2011/0282188 A1 | 11/2011 | Burnside |
| 2011/0295108 A1 | 12/2011 | Cox |
| 2011/0295110 A1 | 12/2011 | Manzke |
| 2012/0016316 A1 | 1/2012 | Zhuang |
| 2012/0071752 A1 | 3/2012 | Sewell |
| 2012/0108950 A1 | 5/2012 | He |
| 2012/0123243 A1 | 5/2012 | Hastings |
| 2012/0130229 A1 | 5/2012 | Zellers |
| 2012/0130230 A1 | 5/2012 | Eichler |
| 2012/0136251 A1 | 5/2012 | Kim |
| 2012/0143055 A1 | 6/2012 | Ng |
| 2012/0150022 A1 | 6/2012 | Bar-Tal |
| 2012/0197108 A1 | 8/2012 | Hartmann |
| 2012/0232380 A1 | 9/2012 | Pelissier |
| 2012/0259209 A1 | 10/2012 | Harhen |
| 2013/0225986 A1 | 8/2013 | Eggers |
| 2013/0296691 A1 | 11/2013 | Ashe |
| 2014/0002063 A1 | 1/2014 | Ashe |
| 2014/0046261 A1 | 2/2014 | Newman |
| 2014/0058221 A1 | 2/2014 | Old |
| 2014/0107475 A1 | 4/2014 | Cox |
| 2014/0228670 A1 | 8/2014 | Justis |
| 2014/0257080 A1 | 9/2014 | Dunbar |
| 2014/0257104 A1 | 9/2014 | Dunbar |
| 2014/0257746 A1 | 9/2014 | Dunbar |

FOREIGN PATENT DOCUMENTS

| | | |
|---|---|---|
| CA | 2 647 432 A1 | 10/2007 |
| CA | 2 659 586 A1 | 12/2007 |
| DE | 10 2008 013 611 A1 | 9/2009 |
| DE | 10 2010 046 948 A1 | 12/2011 |
| EP | 0 488 987 A1 | 6/1992 |
| EP | 0 747 016 A1 | 12/1996 |
| EP | 0 928 976 A2 | 7/1999 |
| EP | 1 212 001 A2 | 6/2002 |
| EP | 1 377 335 A2 | 1/2004 |
| EP | 1 504 713 A1 | 2/2005 |
| EP | 1 715 788 A2 | 11/2006 |
| EP | 1 727 478 A | 12/2006 |
| EP | 1 804 079 A2 | 7/2007 |
| EP | 1 898 775 A2 | 3/2008 |
| EP | 1 913 875 A1 | 4/2008 |
| GB | 2 445 669 A | 7/2008 |
| JP | 2005-312577 A | 11/2005 |
| WO | 96/05768 A1 | 2/1996 |
| WO | 00/63658 A2 | 10/2000 |
| WO | 02/00093 A2 | 1/2002 |
| WO | 2006/078677 A2 | 7/2006 |
| WO | 2006/078678 A2 | 7/2006 |
| WO | 2006/124192 A2 | 11/2006 |
| WO | 2007/025081 A2 | 3/2007 |
| WO | 2008/035271 A2 | 3/2008 |
| WO | 2008/086832 A1 | 7/2008 |
| WO | 2009/070616 A2 | 6/2009 |
| WO | 2009/089280 A1 | 7/2009 |
| WO | 2010/111435 A1 | 9/2010 |
| WO | 2010/132985 A1 | 11/2010 |
| WO | 2011/043874 A1 | 4/2011 |
| WO | 2011/043875 A1 | 4/2011 |
| WO | 2011/044273 A2 | 4/2011 |
| WO | 2011/085034 A1 | 7/2011 |
| WO | 2011/095924 A1 | 8/2011 |
| WO | 2011/098926 A1 | 8/2011 |
| WO | 2011/109249 A1 | 9/2011 |
| WO | 2011/114259 A1 | 9/2011 |
| WO | 2011/123661 A1 | 10/2011 |
| WO | 2011/127191 A1 | 10/2011 |
| WO | 2011150376 A1 | 12/2011 |
| WO | 2012/025854 A1 | 3/2012 |
| WO | 2012040077 A1 | 3/2012 |
| WO | 2012/098483 A1 | 7/2012 |
| WO | 2013034175 A1 | 3/2013 |
| WO | 2014/135592 A1 | 9/2014 |

OTHER PUBLICATIONS

Placidi, Giuseppe, et al.; "Review on Patents about Magnetic Localisation Systems for in vito Catheterizations"; INFM c/o Department of Health Sciences, University of L'Aquila, Via Vetoio Coppito 2, 67100 L'Aquila, Italy; Recent Patents on Biomedical Engineering 2009, 2, 58-64; Received: Dec. 24, 2008; Accepted: Jan. 9, 2009; Revised: Jan. 12, 2009; 8 pages.

Stolowitz Ford Cowger LLP, Listing of Related Cases; Portland, OR; Aug. 19, 2015; 1 page.

Dorveaux et al., "On-the-field Calibration of an Array of Sensors", 2010 American Control Conference, Jun. 30-Jul. 2, 2010, Baltimore, MD, USA, 8 pages.

European Patent Office, "Internaional Search Report" for PCT/EP2011/065420, mailed Aug. 20, 2012, 5 pages.

Stolowitz Ford Cowger LLP, "Listing of Related Cases", Feb. 5, 2014, 2 pages.

* cited by examiner

MAGNETIZATION DEVICE AND METHOD

TECHNICAL FIELD

The present invention relates generally to the field of medical devices and in particular to a device and method for magnetizing a tissue-penetrating medical tool.

BACKGROUND AND OVERVIEW

Unless explicitly indicated herein, the materials described in this section are not admitted to be prior art.

There are numerous medical procedures that involve the insertion of a medical tool or instrument, such as a needle, cannula, catheter or stylet, into a subject's body, e.g. minimally-invasive surgical procedures, local anaesthesia, detection of bio-electrical signals, electrical stimulation for diagnosis or treatment, vascular access, fine needle aspiration, musculoskeletal injections and so on. In such procedures it is generally necessary to guide the medical tool properly to the desired position in the subject's body and it can also be beneficial to monitor or track the medical tool position to ensure that it remains at the desired location. In general it is very difficult for the user to determine the exact position of the tip of the medical tool and thus to be sure whether it is in the desired place, for example adjacent a nerve, or whether it has undesirably penetrated something else, for example a blood vessel.

It has been proposed to use x-ray techniques for needle guidance by providing the clinician with an x-ray image of the needle in the body. However in view of the risks associated with exposure to electromagnetic radiation, it is not possible to provide continuous guidance during insertion of the medical tool and so a series of snapshots are relied upon, which does not give optimal guidance.

More recently the use of ultrasound imaging to guide needle and catheterisation procedures has been proposed. Ultrasound imaging is advantageous compared to x-ray techniques because of the lack of exposure to electromagnetic radiation, and ultrasound probes are easily manipulable to image many different parts of the body. However ultrasound imaging has two main challenges: firstly that the interpretation of ultrasound images is rather difficult, and secondly that needles do not show-up particularly reliably or visibly in the ultrasound image.

As to the problem of needle visibility, the ultrasound image acquisition plane is thin—of the order of 1 mm thick, and so if the needle is out of that plane it will not be imaged. Further, even when the needle is in the imaging plane, because the echogenicity of standard needles is poor at high angles of incidence, the needle may not be particularly visible. It has been proposed to produce echogenic needles which make the needle more visible to ultrasound imaging devices. However these only help when the needle is well-aligned with the imaging plane. Similarly techniques for image processing and ultrasound beam steering help only when the needle is well-aligned with the imaging plane and do not work well for angles of incidence greater than 45 degrees.

Various needle tracking technologies have been proposed based either on a needle guide fitted to an ultrasound probe, e.g. U.S. Pat. No. 6,690,159 B2 or WO-A-2012/040077, or based on the transmission and reception of electromagnetic information, e.g. US-A-2007-027390), but these have functional and accuracy limitations which means that the needle tip position is not exactly known in every clinical circumstance. Typical accuracies are of the order of 2 mm, which can mean the difference between the needle tip being inside or outside a nerve. Further they often require the use of heavily modified or new equipment which is unwelcome to clinicians and to institutions with relatively rigid purchasing regimes.

Most often, therefore, practitioners rely on their skill and experience to judge where the tip of the medical instrument is as it is inserted. They may rely on sound, the touch and feel of the physical resistance to the medical tool and sudden changes in resistance, and changes in resistance to the injection of air or fluids. Developing this level of skill and experience is time-consuming and difficult and as there is an anatomical variation from patient to patient, the procedures inevitably entail some risks.

More recently it has been proposed to utilise magnetic tracking of a needle or other tissue-penetrating tool using a magnetometric detector attached to a freehand ultrasound probe and using a magnetised tissue-penetrating tool. Such a technique is described in our co-pending International patent application no. PCT/EP2011/065420. In this system a standard freehand ultrasound probe has a magnetometric detector attached to it, the detector comprising an array of magnetometric sensors. The sensors detect the magnetic field from the magnetised tissue-penetrating medical tool and send their readings of the magnetic field to a base station. The base station includes a data processor for calculating from the measurements the relative position and orientation of the tissue-penetrating medical tool relative to the ultrasound probe. The base station can supply this calculated position and orientation to the ultrasound imaging system so that the tissue-penetrating medical tool can be displayed on the ultrasound image of the subject's anatomy.

The system is advantageous in that it allows the operator to see both the ultrasound imaged anatomy and the magnetically detected tissue-penetrating medical tool on the same image. This enables greater accuracy in the procedure. Further, the attachment of a magnetometric detector to the ultrasound probe does not alter the feel of the ultrasound probe significantly, and it remains, therefore, familiar to the practitioner. Similarly the magnetization of the tissue-penetrating medical tool does not alter its physical characteristics, again, preserving the familiarity and experience of the clinician. The system is also simple and cheap compared to optical or electromagnetic tracking technologies and because the ultrasound probe can be manipulated freely, the ease-of-use of the freehand ultrasound system is preserved.

The system requires, however, that the tissue-penetrating medical tool is reliably and consistently magnetised.

Accordingly the present invention provides a device and method for magnetising a tissue-penetrating medical tool. In particular at least part of the tissue-penetrating medical tool is magnetically saturated by the magnetization device and method. The device and method preserve the sterility of the tool while reliably magnetising the tool to the extent necessary. The device and method may also be adapted to magnetise a defined length of the tissue-penetrating medical tool.

In more detail one embodiment of the invention provides a device for magnetizing a tissue-penetrating medical tool comprising a tool-receiving space for receiving at least part of the tissue-penetrating medical tool; a magnetic flux generator generating a magnetic field, the magnetic field having a magnetization region for magnetically-saturating the part of the tissue-penetrating medical tool which is in said tool-receiving space, the magnetic flux in the magnetization region being oriented in a direction substantially parallel to a longitudinal axis of the tissue-penetrating medical tool.

Another aspect of the invention provides a method of magnetising a tissue-penetrating medical tool comprising: positioning at least part of the tissue-penetrating medical tool in a tool-receiving space; generating a magnetic field in said tool-receiving space to magnetically-saturate the part of the tissue-penetrating medical tool which is in said tool-receiving space, the magnetic flux in the magnetization region being oriented in a direction substantially parallel to a longitudinal axis of the tissue-penetrating medical tool.

Preferably the tool receiving space is adapted to permit movement of the tissue-penetrating medical tool in a movement direction parallel to the longitudinal axis of the tissue-penetrating medical tool. Preferably the tool-receiving space is adapted to admit a predefined length of the tissue-penetrating medical tool, and more preferably to allow it to be moved into and out of the tool-receiving space in opposing movement directions. The tool-receiving space may have a longitudinal axis substantially parallel to the longitudinal axis of the tool and substantially parallel to the magnetic flux in the magnetisation region.

The magnetic flux generator may be provided on one side of the tool-receiving space. More preferably the magnetic flux generator is provided on two sides of the tool-receiving space. Alternatively the magnetic flux generator may surround the tool-receiving space, e.g. by having a cylindrical configuration.

The magnetic flux generator may comprise a stationary part and a movable part, the stationary part generating a magnetic field extending through the magnetization region and the moveable part being movable towards and away from the magnetization space so that its magnetic field is selectively applied to the magnetization region. The movable part of the magnetic flux generator may comprise a plurality of magnets positioned along a direction parallel to the longitudinal axis of the tissue-penetrating medical tool. The plurality of magnets may have alternating pole orientations. Preferably the plurality of magnets comprise a first set of magnets with alternating poles on one side of the magnetization region and a second set of magnets on the opposite side of the magnetization region, the second set of magnets having the same pole orientations as the first set.

Preferably the movable part of the magnetic flux generator is movable towards and away from the magnetization region in a direction transverse to the longitudinal axis of the tissue-penetrating medical tool.

The tool receiving space may be constituted by a longitudinally-extending space.

The magnetic flux generator may be a permanent magnet or electromagnet.

A conveyor belt may be provided to convey a tissue-penetrating medical tool through the magnetization region in the tool-receiving space. Where an electromagnetic and conveyor belt are used together, the electromagnetic may be controlled to vary the strength and/or direction of the magnetic flux in the magnetization region as the tissue-penetrating tool passes through the magnetization region. Preferably an optical sensor is provided to detect the position of the tissue-penetrating tool as it passes through the magnetization region.

The tool-receiving space may have one open end for receiving the tool and a closed end, the length of the tool-receiving space thus defining a length of tissue-penetrating medical tool which is within the magnetization region.

The tool-receiving space may comprise a sterile liner such as a disposable drape and/or disposable plastics tube. The disposable plastics tube may be a standard needle or cannula cover.

In one embodiment the device is sterile and, optionally, disposable.

The device is preferably hand-held and optionally is provided with a guard extending around the entrance to the tool-receiving space to protect the user's hand. The guard may be a plastics shroud or protective lip.

The tissue-penetrating medical tool can be a needle, cannula, stylet, or the like.

BRIEF DESCRIPTION OF THE DRAWINGS

The invention will be further described by way of examples with reference to the accompanying drawings in which.

DETAILED DESCRIPTION

Figure 1:
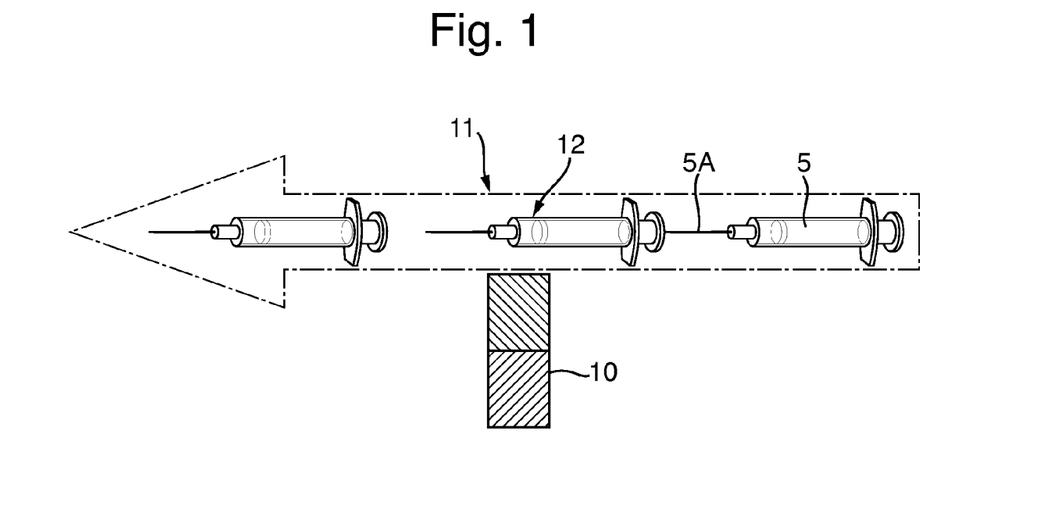
FIG. 1 schematically illustrates a first embodiment of the present invention.

FIG. 1 schematically illustrates a first embodiment of the invention. In FIG. 1 the tissue-penetrating medical tool is a hypodermic needle 5A forming part of a hypodermic syringe 5. The magnetization device comprises a magnetic flux generator 10, which can be a permanent magnet or electromagnet, which generates magnetic flux in a magnetization region 12 in a tool-receiving space 11 through which the hypodermic syringe 5 can be passed. The magnetic field generated in the magnetization region 11 is sufficiently strong to saturate the magnetic properties of the metallic needle 5A. In this embodiment the tool is passed over one pole of the magnetic flux generator, in one direction only, magnetising the entire length of the tool 5A.

Advantages of this embodiment are that it is simple and easy to use and that the needle 5A can remain in its sterile package while being magnetised.

Figure 2:
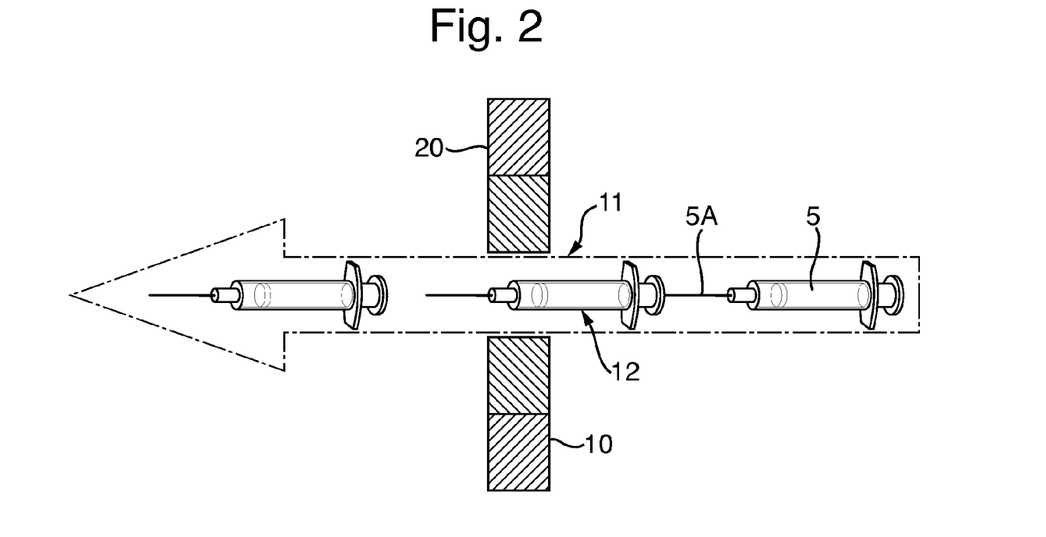
FIG. 2 schematically illustrates a second embodiment of the present invention.

FIG. 2 schematically illustrates a second embodiment of the invention which is similar to that of FIG. 1 but in which the magnetic flux generator 10, 20 extends around the tool-receiving space 11 and magnetization region 12. This can be achieved by providing a second permanent magnet 20 on the opposite side of the tool-receiving space 11, or by using a cylindrical permanent magnet surrounding the tool-receiving space 11 with its longitudinal axis parallel to the longitudinal axis of the tissue-penetrating medical tool 5A. Alternatively the magnets 10 and 20 can be replaced by one or more electromagnets. It should be noted that in the case of using two permanent magnets 10 and 20 the magnets are oriented with their poles in opposite directions such that like poles face each other across the tool-receiving space 11. This creates a magnetic field in the tool-receiving space 11 which is parallel to the longitudinal axis of the tissue-penetrating medical tool 5A.

In the embodiment of FIG. 2, the entire hypodermic syringe 5 can be passed through the tool-receiving space 11 in one direction, resulting in magnetization of the entire length of the needle 5A.

As with the first embodiment the magnetic flux generator generates a field which is sufficient to saturate the magnetic properties of the metallic tool 5A. The second embodiment has advantages over the first embodiment that a stronger magnetic field can be generated in the magnetization region which gives more consistent magnetization of the tool.

Figure 3:
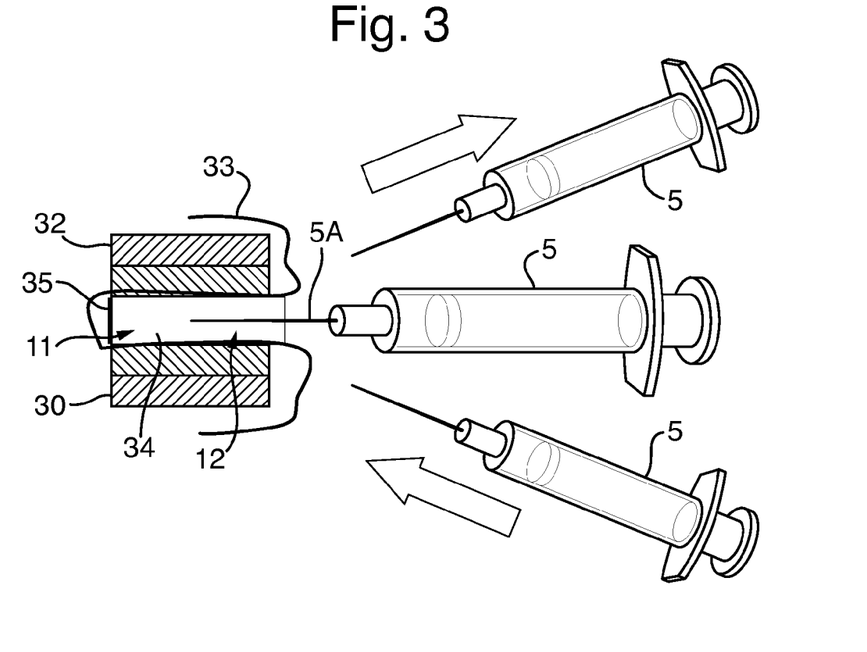
FIG. 3 schematically illustrates a third embodiment of the present invention.

FIG. 3 schematically illustrates a third embodiment of the invention. In the FIG. 3 device the magnetizer comprises a magnetic flux generator formed from two permanent magnets 30 and 32, or alternatively one cylindrical magnet or an electromagnet arrangement which defines a cylindrical tool-receiving space 11. The magnetic flux generator 30, 32 generates a magnetic field in the tool-receiving space 11 which thus constitutes a magnetization region 12 and the magnetic field is oriented parallel to the longitudinal axis of the tool-receiving space 11.

The magnetizer device also includes a sterile plastics tube 34, which can be the same type of tube as commonly used as a disposable needle cover, and, in addition, a flexible sterile drape 33 may be provided which covers the magnetic flux generator and extends into the tool-receiving space before the plastics tube 34 is inserted into it. The plastics tube 34 preferably has a bottom wall 35 which forms a closed end of the tool-receiving space 11.

In use, the tissue-penetrating medical tool 5A is passed into the plastics tube 34 until its tip touches the bottom wall 35. This defines a length of the tool which is in the magnetization region 12. After a few seconds the tool is removed and the part of the tool which was in the magnetization region will have been magnetised. As with the embodiments above the magnetic flux generator 30, 32 generates a sufficient strength of magnetic field to saturate the magnetic material of the tool.

The third embodiment has advantages that a strong magnetic field can be generated in the magnetization region and because a defined length of the tool is magnetised, better tracking results can be achieved by the magnetic tracking system.

Figure 4:
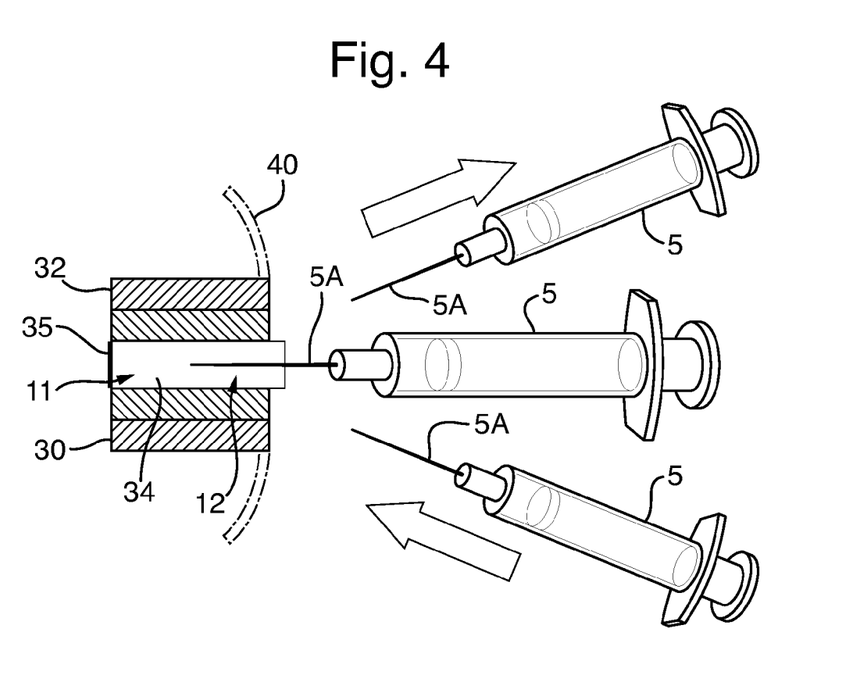
FIG. 4 schematically illustrates a fourth embodiment of the present invention.

FIG. 4 illustrates a fourth embodiment of the invention which is similar to the third embodiment except that the whole magnetizer is sterile and thus the flexible sterile drape 33 can be omitted. With the exception of the need to position such a flexible drape in the tool-receiving space before insertion of the plastics tube 34, the use of the FIG. 4 embodiment is the same as that of the FIG. 3 embodiment.

Figure 5:
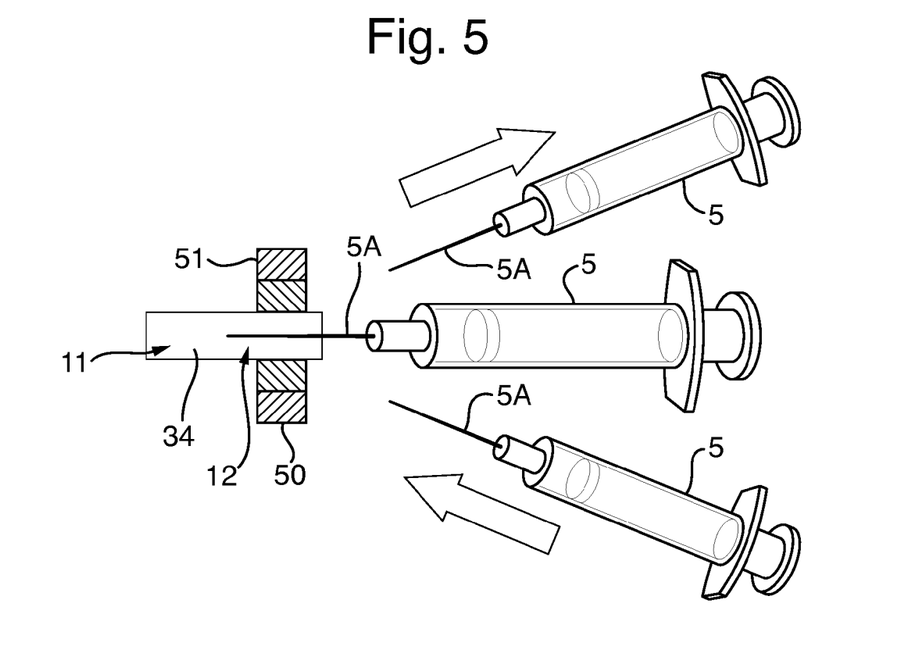
FIG. 5 schematically illustrates a fifth embodiment of the present invention.

FIG. 5 illustrates a fifth embodiment of the invention. The magnetization device of FIG. 5 comprises a magnetic flux generator formed from two permanent magnets 50 and 51, or alternatively a single cylindrical permanent magnet or electromagnet and a plastics tube 54 defining a tool-receiving space 11 extending through the magnetization region 12 of the magnetic flux generator. As illustrated the plastics tube 54 is longer than the magnetization region 12. The tube 54 can be a sterile plastics tube of the same type as used for needle covers in needle packages. In the FIG. 5 embodiment the tube 54 is open at both ends, but the length of the tissue-penetrating medical tool 5A which is magnetised is defined by the position of the magnetic flux generator 50, 51 in relation to the entry end of the tube 54. Thus introducing the exemplified needle 5A into the tube until the body of the syringe contacts the entry end of the tube 54 means that a defined length of the needle 5A from its distal tip is passed through the magnetization region 12.

The magnetic flux generator 50, 51 can be a permanent magnet or magnets which are small and thus of low cost. The device may, therefore, be completely sterile and completely disposable. As with the previous embodiments the magnetic flux generator 50, 51 generates a magnetic field which is strong enough to saturate the magnetic properties of the tool 5A.

The embodiment of FIG. 5 is suitable for inclusion as an integral part of the a medical device package. That is to say the device can be supplied with the tissue-penetrating medical tool extending already into the tool-receiving space 11 so that when the user extracts the device for use, the required defined extent of the tissue-medicating tool 5A is magnetised.

Figure 6:
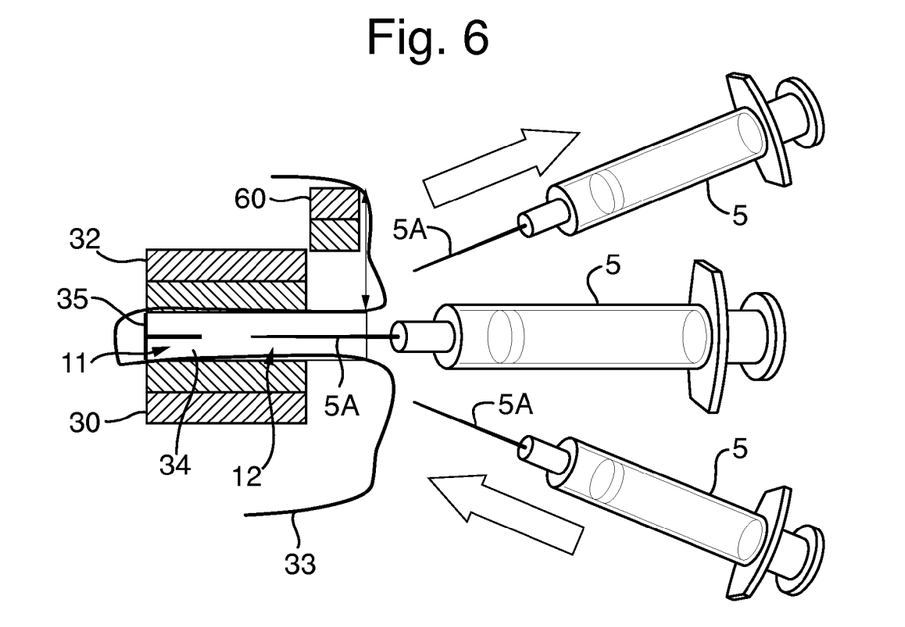
FIG. 6 schematically illustrates a sixth embodiment of the present invention.

FIG. 6 illustrates a modification applied to the third embodiment described above in which like parts are indicated with the same reference numerals. The FIG. 6 embodiment includes in the magnetic flux generator an additional magnet 60 which is a permanent magnet, with its pole orientation reversed compared to the magnets 30 and 32. The magnet 60 is movable towards and away from the axis of the tissue-penetrating medical tool 5A and tool-receiving space 11 transverse to their longitudinal axes. In use the tissue-penetrating medical tool 5A is introduced into the tool-receiving space 11 as before and after a few seconds the additional magnet 60 is moved back and forth one or more times before the tool is removed from the magnetization device. The effect of moving the magnet 60 into and then out of the vicinity of the magnetization region 12 is that it sharpens the magnetic pole which is formed in the tissue-penetrating medical tool 5A at its proximal end which gives better results in magnetic needle tracking. By "sharpening the pole" is meant that the magnetization of the tissue-penetrating medical tool is restricted more clearly to a defined length, i.e. the magnetization falls-off at the proximal end of the tool. This is achieved by the mini-dipoles in the magnetic material of the tool being aligned by the flux in the magnetisation region but stop aligning abruptly at the proximal end because of the influence of the additional magnet 60. This creates a sharper pole than the spherical pole at the other (tip) end created by the mini-dipoles being aligned right up to the abrupt physical tip of the tool 5.

Although the additional magnet 60 is illustrated as applied to the third embodiment of the invention, it will be appreciated that it can be added to the first, second, fourth or fifth embodiments in just the same way.

Figure 7:
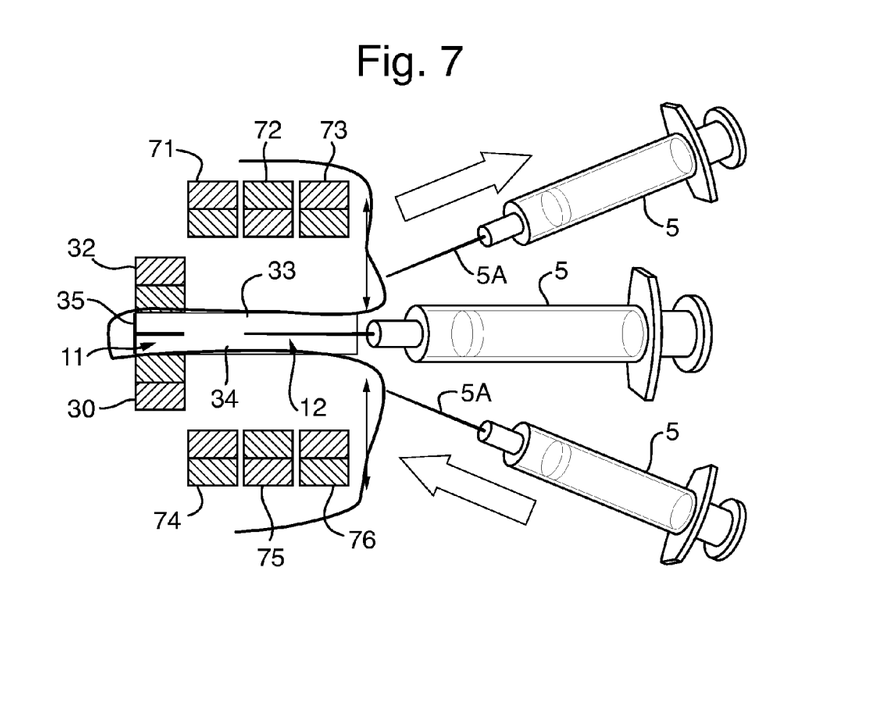
FIG. 7 schematically illustrates a seventh embodiment of the present invention.

FIG. 7 illustrates a seventh embodiment of the invention. This is an enhancement of the FIG. 6 embodiment in that more movable magnets are provided as part of the magnetic flux generator. Thus in this embodiment the fixed magnets 30, 32 are shorter compared to the plastics tube 34, while three additional magnets 71-76 are provided on each side of the remaining extent of the plastics tube 34. The magnets 71-76 are movable towards and away from the tool-receiving space 11 in a direction transverse to the longitudinal axis of the space and the tissue-penetrating medical tool 5A. As illustrated the fixed magnets 30 and 32 have like poles facing each other across the tool-receiving space 11 whereas the pairs of magnets 71 and 74, 72 and 75, 73 and 76 which face each other across the tool-receiving space have opposite poles facing each other. In addition, movable magnets down each side of the tool-receiving space 11 have alternating pole orientations. Thus, in the illustrated example, the magnets 71 and 73 have their poles oriented in the same direction as the fixed magnet 32 on the same side of the tool-receiving aperture whereas the magnet 72 between them is oppositely oriented. On the other side of the tool-receiving space 11 the magnets 74 and 76 are oppositely oriented from the fixed magnet 30, while the magnet 75 between them is oriented in the same way as the fixed magnet 30.

The reason for including the alternately oriented magnets 71 to 76 is to introduce multiple poles into the tissue-penetrating medical tool 5A and thus effectively "code" the tool so that it can be recognised and identified by the magnetic tracking system. Thus to use the magnetizer device the exemplified needle 5A is passed into the tube 34 until its tip touches the closed bottom 35. After a few second the movable magnets 71 to 76 are moved back and forth once, or more than once, as indicated by the arrows and the needle is then removed from the tube 34. Only the length of the needle which has been in the magnetization region 12 will be magnetised and multiple poles will have been introduced into the needle.

Although the modification of FIG. 7 is illustrated as applied to the FIG. 3 embodiment, it can be applied to the embodiments of FIGS. 1, 2, 4 and 5.

Figure 8:
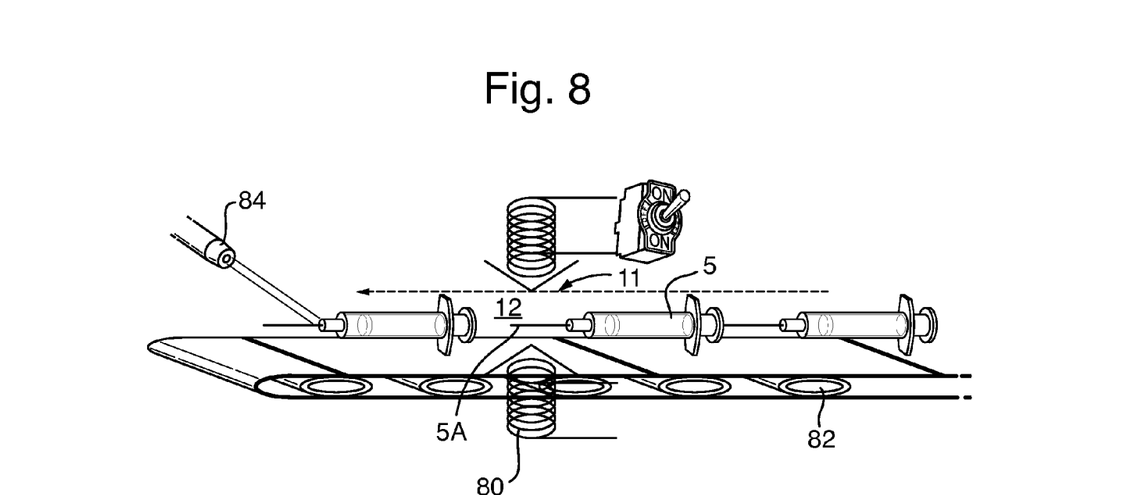
FIG. 8 schematically illustrates an eighth embodiment of the present invention.

FIG. 8 illustrates a seventh embodiment of the invention. In FIG. 8 the magnetic flux generator is an electromagnetic 80 which can comprise a pair of Helmholtz coils to generate a uniform magnetic field in a magnetization region 12. A conveyor belt 82 is provided to move the tissue-penetrating medical tool such as a needle 5A attached to a syringe 5 through a tool-receiving space 11. An optical sensor 84 is provided to detect the position of the tissue-penetrating medical tool 5A and a control system (not illustrated) is used to control the conveyor belt 82 and electromagnet 80 in response to the optical sensor 84 to switch the magnetic field generated by the electromagnet on or off, or to vary its strength, depending on the position of the tissue-penetrating medical tool. The magnetizer device of FIG. 8 is thus able to magnetise the tool as desired. The tool may be completely and uniformly magnetised, or a defined partial length can be magnetised, and/or the magnetization can be varied along the extent of the tool to provide a coding of the tool.

As with the previous embodiment the electromagnet 80 is controlled to generate a magnetic field which is strong enough to saturate the magnetic properties of the needle.

The embodiment of FIG. 8 is therefore advantageous in being able to create complex coding on any type of magnetisable tissue-penetrating medical tool.

In a variation of the FIG. 8 embodiment, rather than providing a conveyor belt 82, multiple electromagnetic coils 80 may be provided along the length of the needle with the multiple coils being selectively energised to magnetically code the needle.

The magnetizer embodiments of FIGS. 1 to 7 are preferably constructed as hand-held devices with an ergonomic design. A protective lip or shroud may be provided around the entry opening of the tool-receiving space 11 and extending radially outwards from the device to protect the hand of the user as they insert the needle into the tool-receiving space. Such a shroud 40 is illustrated schematically in dotted form in FIG. 4. The shroud or hand guard may be made of rigid of semi-rigid plastics material.

The magnetizer embodiments of FIGS. 1 to 7 may be supplied as part of a pack with tissue-penetrating tools.

The invention claimed is:

1. A device for magnetizing a tissue-penetrating medical tool comprising:
 a tool-receiving space having a closed end, an open end, and a sterile liner, and being of a length to receive within the sterile liner at the open end a predefined length of the tissue-penetrating medical tool; and
 a magnetic flux generator generating a magnetic field, the magnetic field having a magnetization region for magnetically-saturating the part of the tissue-penetrating medical tool which is in said tool-receiving space, the magnetic flux in the magnetization region being oriented in a direction substantially parallel to a longitudinal axis of the tissue-penetrating medical tool.

2. The device according to claim 1, wherein the tool-receiving space is adapted to permit movement of the tissue-penetrating medical tool in the tool-receiving space in a movement direction parallel to the longitudinal axis of the tissue-penetrating medical tool.

3. The device according to claim 1, wherein the tool-receiving space is adapted to permit movement of the tissue-penetrating medical tool into and out of the tool-receiving space.

4. The device according to claim 1, wherein the magnetic flux generator is provided on one side of the tool-receiving space.

5. The device according to claim 1, wherein the magnetic flux generator is provided on two sides of the tool-receiving space.

6. The device according to claim 1, wherein the magnetic flux generator is provided to surround the tool-receiving space.

7. The device according to claim 1, wherein the magnetic flux generator is adapted to generated magnetic fields oriented perpendicular to each other and extending into the magnetization region.

8. The device according to claim 1, wherein the magnetic flux generator further comprises a movable magnet which can be moved towards and away from the tool-receiving space.

9. The device according to claim 8, wherein plural movable magnets are provided.

10. The device according to claim 9, wherein the plural movable magnets have oppositely oriented poles.

11. The device according to claim 8, wherein the movable magnet is movable transverse to the longitudinal axis of the tool-receiving space.

12. The device according to claim 1, wherein a conveyor belt is provided to convey a tissue-penetrating medical tool into the tool-receiving space.

13. The device according to claim 1, wherein the magnetic flux generator is an electromagnet.

14. The device according to claim 13, further comprising a controller to control the electromagnet to vary at least one of the strength and direction of the magnetic field in the magnetization region.

15. The device according to claim 14, further comprising an optical sensor adapted to detect the position of the tissue-penetrating medical tool and to supply the detected position to the controller.

16. The device according to claim 1, wherein the sterile liner is made from plastics.

17. The device according to claim 1, wherein the sterile liner is disposable.

18. The device according to claim 1, wherein the sterile liner is a needle cover.

19. The device according to claim 1, wherein the sterile liner is a disposable drape.

20. The device according to claim 1, which is sterile.

21. The device according to claim 1, which is disposable.

22. The device according to claim 1, wherein a protective hand guard is provided around the tool-receiving space.

23. The device according to claim 1, including a tissue-penetrating medical tool which is a needle, cannula, stylet or catheter.

24. A method of magnetizing a tissue-penetrating medical tool comprising:
 positioning at least part of the tissue-penetrating medical tool in a tool-receiving space, the tool-receiving space having a closed end, an open end, and a sterile liner, and being of a length to receive within the sterile liner at the open end a predefined length of the tissue-penetrating medical tool; and generating a magnetic field in said tool-receiving space to magnetically-saturate the part of the tissue-penetrating medical tool which is in said tool-receiving space, the magnetic flux in the magnetization region being oriented in a direction substantially parallel to a longitudinal axis of the tissue-penetrating medical tool.

25. The method according to claim 24, further comprising the step of moving the tissue-penetrating medical tool into the tool-receiving space in a movement direction parallel to the longitudinal axis of the tissue-penetrating medical tool.

26. The method according to claim 24, further comprising the step of moving the tissue-penetrating tool into and out of the tool-receiving space.

27. The method according claim 24, further comprising the step of bringing a movable magnet closer to and further away from the tool-receiving space to modify the magnetization of the tissue-penetrating medical tool.

28. The method according to claim 24, wherein the magnetic flux generator is an electromagnet and further comprising the step of controlling the electromagnet to vary at least one of the strength and direction of the magnetic flux in the magnetization space as the tissue-penetrating medical tool is passed through the magnetization space.

29. The method according to claim 24, comprising using a device for magnetizing a tissue-penetrating medical tool comprising: a tool-receiving space for receiving at least part of the tissue-penetrating medical tool; a magnetic flux generator generating a magnetic field, the magnetic field having a magnetization region for magnetically-saturating the part of the tissue-penetrating medical tool which is in said tool-receiving space, the magnetic flux in the magnetization region being oriented in a direction substantially parallel to a longitudinal axis of the tissue-penetrating medical tool.

* * * * *